United States Patent
Hague et al.

(10) Patent No.: US 10,851,070 B2
(45) Date of Patent: *Dec. 1, 2020

(54) PROCESSES FOR THE RESOLUTION OF BENZODIAZEPIN-2-ONE AND BENZOAZEPIN-2-ONE DERIVATIVES

(71) Applicant: Enanta Pharmaceuticals, Inc., Watertown, MA (US)

(72) Inventors: Andrew Hague, Chelmsford, MA (US); Matthew Ronsheim, Sudbury, MA (US)

(73) Assignee: Enata Pharmaceuticals, Inc., Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/683,303

(22) Filed: Nov. 14, 2019

(65) Prior Publication Data

US 2020/0157057 A1    May 21, 2020

Related U.S. Application Data

(63) Continuation of application No. 16/188,954, filed on Nov. 13, 2018, now Pat. No. 10,501,422.

(60) Provisional application No. 62/585,192, filed on Nov. 13, 2017.

(51) Int. Cl.
| | | |
|---|---|---|
| *C07D 401/12* | (2006.01) | |
| *C07D 401/14* | (2006.01) | |
| *C07D 403/12* | (2006.01) | |
| *C07D 409/14* | (2006.01) | |
| *C07D 413/14* | (2006.01) | |
| *C07D 417/14* | (2006.01) | |
| *C07D 243/26* | (2006.01) | |
| *C07B 57/00* | (2006.01) | |

(52) U.S. Cl.
CPC ............ *C07D 243/26* (2013.01); *C07B 57/00* (2013.01); *C07B 2200/07* (2013.01)

(58) Field of Classification Search
CPC .. C07D 401/12; C07D 401/14; C07D 403/12; C07D 409/14; C07D 413/14; C07D 417/14
See application file for complete search history.

(56) References Cited

FOREIGN PATENT DOCUMENTS

WO    WO 2011151651    * 12/2011

* cited by examiner

*Primary Examiner* — Bruck Kifle
(74) *Attorney, Agent, or Firm* — Edgar W. Harlan; Carolyn S. Elmore; Elmore Patent Law Group, P.C.

(57) ABSTRACT

The present invention relates to processes and intermediates useful in the preparation of biologically active molecules, especially in the synthesis of Respiratory Syncytial Virus (RSV) inhibitors. The present invention also relates to processes and intermediates for the preparation of compounds of Formula (I-0) and Formula (I):

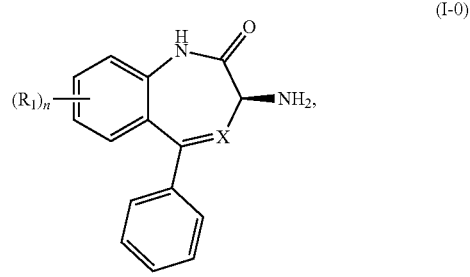

(I-0)

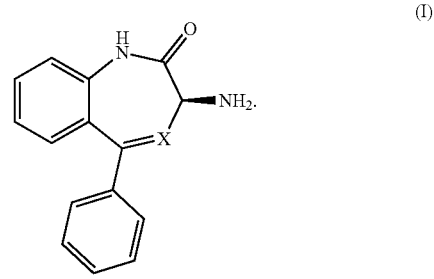

(I)

15 Claims, No Drawings

PROCESSES FOR THE RESOLUTION OF BENZODIAZEPIN-2-ONE AND BENZOAZEPIN-2-ONE DERIVATIVES

RELATED APPLICATIONS

This application is a continuation application of U.S. application Ser. No. 16/188,954, filed Nov. 13, 2018, which claims the benefit of U.S. Provisional Application No. 62/585,192, filed on Nov. 13, 2017. The entire teachings of the above applications are incorporated herein by reference.

TECHNICAL FIELD

The present invention describes the crystallization induced dynamic resolution of 3-amino-1,3-dihydro-2H-benzo[1,4]-diazepin-2-one, 3-amino-1,3-dihydro-2H-benzo[b]azepine-2-one and derivatives thereof whereby the racemic precursor is converted to a single enantiomer. These are useful intermediates in the synthesis of biologically active molecules, in particular for those that inhibit Respiratory Syncytial Virus (RSV).

BACKGROUND OF THE INVENTION

Human respiratory syncytial virus (HRSV) is a negative-sense, single stranded, RNA paramyxovirus (KM. Empey, et al., *Rev. Anti-Infective Agents*, 2010, 50(1 May), 1258-1267). RSV is a major cause of respiratory illness in patients of all ages. In adults, it tends to cause mild cold symptoms. In school-aged children, it can cause a cold and bronchial cough. However, in infants and toddlers the virus can cause lower respiratory tract infections including bronchiolitis (inflammation of the smaller airways of the lungs) or pneumonia with many of them requiring hospitalization. It has also been found to be a frequent cause of middle ear infections (otitis media) in pre-school children. RSV infection in the first year of life has been implicated in the development of asthma during childhood.

There are known high-risk groups that infection with RSV is more likely to progress into the acute lower respiratory tract infections (ALRI). Premature infants and/or infants suffering from lung or cardiac disease are at the highest risk to develop ALRI. Additional high-risk groups include the elderly, adults with chronic heart and/or lung disease, stem cell transplant patients and the immunosuppressed.

Currently, there is no vaccine available to prevent HRSV infection. Palivizumab is a monoclonal antibody that is used prophylactically to prevent HRSV infection in high risk infants, e.g. premature infants, and infants with cardiac and/or lung disease. The high cost of Palivizumab treatment limits its use for general purposes. Ribavirin has also been used to treat HRSV infections, but its effectiveness is limited. There is a major medical need for new and effective HRSV treatments that can be used generally by all population types and ages.

There have been several RSV fusion inhibitors that have been disclosed in the following publications: WO2010/103306, WO2012/068622, WO2013/096681, WO2014/060411, WO2013/186995, WO2013/186334, WO 2013/186332, WO 2012 080451, WO 2012/080450, WO2012/080449, WO 2012/080447, WO 2012/080446, and *J. Med. Chem.* 2015, 58, 1630-1643. Examples of other N-protein inhibitors for treatment of HRSV have been disclosed in the following publications: WO 2004/026843, WO2017/015449, *J. Med. Chem.* 2006, 49, 2311-2319, and *J. Med. Chem.* 2007, 50, 1685-1692. Examples of L-protein inhibitors for HRSV have been disclosed in the following publications: WO2017/123884, WO 2011/005842, WO 2005/042530, *Antiviral Res.* 2005, 65, 125-131, and *Bioorg. Med. Chem. Lett.* 2013, 23, 6789-6793. Examples of nucleosides/polymerase inhibitors have been disclosed in the following publications: WO 2013/242525 and *J. Med. Chem.* 2015, 58, 1862-1878.

There is a need for the development of effective treatments for HRSV. Particular, benzodiazepine derivatives are known to be active against RSV. Research has shown that activity resides in one enantiomer of a racemic mixture. Most previously known synthetic routes to the active isomer employ conventional resolution techniques, i.e. treatment with a chiral acid and separation of the diastereoisomeric salt by crystallization or chromatography, but this is impractical on an industrial scale because typically 50% of the undesired enantiomer is discarded unless there is a method to recycle it. In recent years several groups have utilized the approach first published in 1987 by Merck that demonstrated that the mixture of diastereoiosomeric salts could undergo spontaneous racemization in-situ by treating with a catalytic amount of an aromatic aldehyde such as 3,5-dichlorosalicylaldehyde, resulting in a crystallization induced dynamic resolution of the racemate to afford a single enantiomer, Reider, P. J.; Davis, P.; Hughes, D. L.; Grabowski, E. J. J. *J. Org. Chem.* 1987, 52, 955. A significant proportion of the examples reported in the literature employing either approach (described above) rely on the amide nitrogen being protected prior to the resolution and subsequently de-protected later in the synthesis thereby decreasing the efficiency of the overall process. (WO 2005/090319 A1).

Examples where the resolution is conducted on derivatives with an unprotected amide are limited and require conducting the resolution at elevated temperature. BMS reported in 2016 (OPRD) such an example, resolution of a benzoazepin-6-one conducted in aq. toluene at 100° C. for 12 hours in the presence of catalytic 3,5-dichlorosalicylaldehyde. Merck reported in 1994 (Armstrong, III, J. D.; Eng, K. K.; Keller, J. L.; Purick, R. M.; Hartner, Jr., F. W.; Choi, W-B.; Askin, D.; Volante, R. P., *Tetrahedron Letters*, 1994, 35, 3239-3242) the resolution of a benzoazepin-2-one in aq. isopropanol at 70° C. for 120 hours with catalytic 5-nitrosalicylaldehyde. There is a need for more efficient and milder ways to resolve the active benzodiazepine from its racemate.

SUMMARY OF THE INVENTION

In certain embodiments, the present invention provides methods for preparing a compound of Formula (I-0):

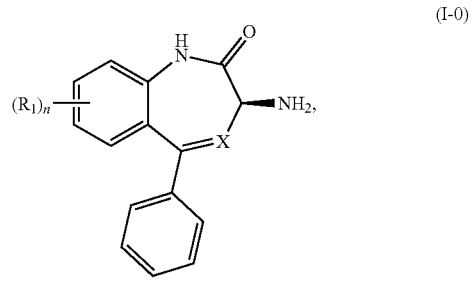

wherein X is N or CH; $R_1$ is halogen, CN or optionally substituted $C_1$-$C_3$ alkyl; and n is 0, 1, 2 or 3. Preferably n is 0.

A preferred embodiment of a compound of Formula (I-0) is a compound of Formula (I):

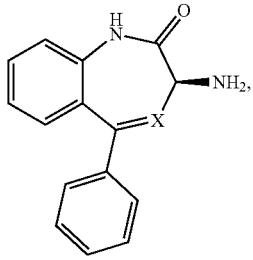
(I)

wherein X is as previously defined.

Another preferred embodiment of a compound of Formula (I-0) is the compound of Formula (Ia):

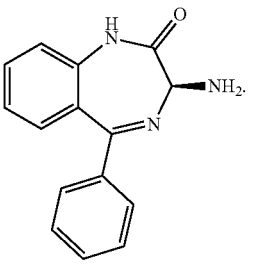
(Ia)

Another preferred embodiment of a compound of Formula (I-0) is the compound of Formula (Ib):

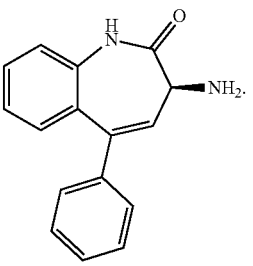
(Ib)

The invention relates to the preparation of chiral compounds of Formula (I-0), (I), (Ia), or (Ib) in substantially enantiomerically pure form, employing derivatives of tartaric acid as the chiral resolving agent under mild reaction conditions without the need to protect and subsequently de-protect the lactam nitrogen.

The invention further relates to methods for increasing product yield and chiral purity and decreasing the number of process steps for intermediate and large scale production of the compounds of Formula (Ia) and (Ib). Such compounds are useful as intermediates in the synthesis of RSV inhibitors, such as those disclosed in WO2017/015449 A1.

DETAILED DESCRIPTION OF THE INVENTION

In its principal embodiment, the present invention provides a process for producing a compound of Formula (I-0):

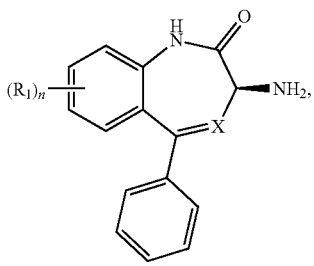
(I-0)

wherein X is N or CH; $R_1$ is halogen, CN or optionally substituted $C_1$-$C_3$ alkyl; and n is 0, 1, 2 or 3. Preferably n is 0. Preferred substituents on the alkyl groups include halogen, such as fluoro or chloro.

In one embodiment, the process of the invention comprises the steps of
(1) reacting a compound of Formula (I'-0),

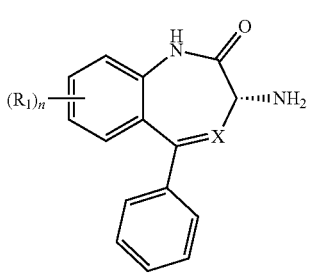
(I'-0)

wherein X, $R_1$, and n are as previously defined, with a compound of Formula (III),

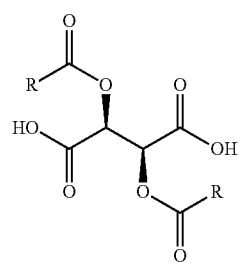
(III)

wherein R is optionally substituted phenyl, to yield a salt of Formula (IV-0),

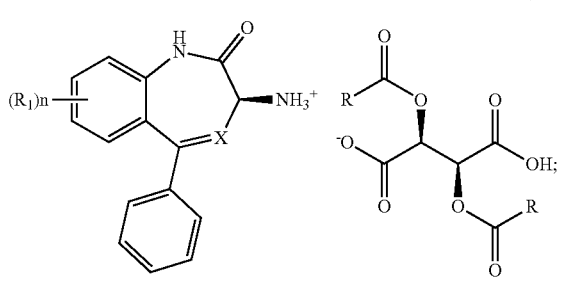
(IV-0)

and (2) treating the salt of Formula (IV-0) with a base to provide the compound of Formula (I-0).

In another embodiment, the present invention provides a process for the preparation of a compound of Formula (I'-0):

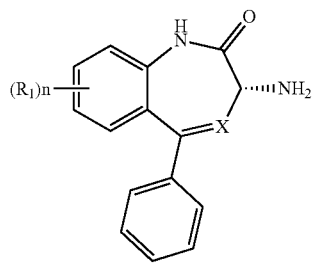

wherein X is N or CH; $R_1$ is halogen, CN or optionally substituted $C_1$-$C_3$ alkyl; and n is 0, 1, 2 or 3. The process comprises the steps of (1') reacting a compound of Formula (I-0),

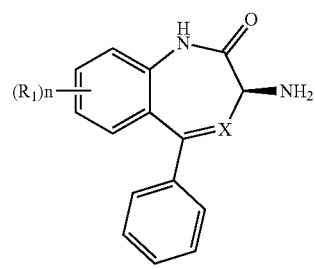

with a compound of Formula (III'),

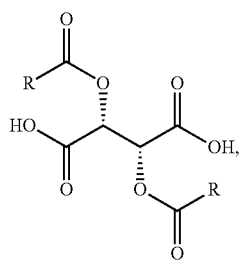

wherein R is previously defined to yield a salt of Formula (IV'-0),

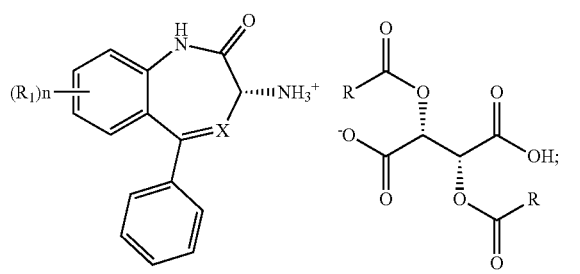

and (2') treating the salt of Formula (IV'-0) with a base to provide the compound of Formula (I'-0).

In one embodiment, the starting compound of step (1) or (1') is present in a racemic mixture with its enantiomer. In another embodiment, the starting compound of step (1) or (1') is present in a mixture with its enantiomer, wherein one of the two enantiomers is in enantiomeric excess, for example, an enantiomeric excess of at least 5, 10, 20, 30, 40, 50, 60, 70, 80 or 90%. In another embodiment, the starting compound of step (1) or (1') is present in a substantially pure form, i.e., in an enantiomeric excess of at least 90%, 95% or 99%.

Preferably, the starting compound of step (1) or step (1') is present in a racemic mixture with its enantiomer.

In one embodiment, the invention provides a method for producing a compound of Formula (I-0), comprising the steps of (a) reacting a racemic mixture of the compound of Formula (I-0) and a compound of Formula (I'-0), wherein X in the compound of Formula (I-0) and Formula (I'-0) are the same, with a compound of Formula (III) to yield a salt of Formula (IV-0); and (b) treating the salt of Formula (IV-0) with a base to provide the compound of Formula (I-0).

In another embodiment, the invention provides a method for producing a compound of Formula (I'-0), comprising the steps of (a') reacting a racemic mixture of the compound of Formula (I'-0) and a compound of Formula (I-0), wherein X in the compound of Formula (I-0) and Formula (I'-0) are the same, with a compound of Formula (III') to yield a salt of Formula (IV'-0); and (b') treating the salt of Formula (IV'-0) with a base to provide the compound of Formula (I'-0).

Preferably, the desired enantiomer is present in the product in an enantiomeric excess, for example an enantiomeric excess of at least 70%, at least 80%, or at least 85%. Preferably, the product is substantially enantiomerically pure, i.e., in an enantiomeric excess of at least 90%, at least 95% or at least 99%.

In one embodiment, the present invention provides a process for producing a compound of Formula (I):

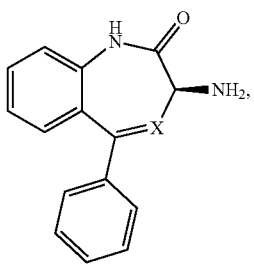

wherein X is as previously defined.

The process comprises the steps of
(1) reacting a compound of Formula (I'),

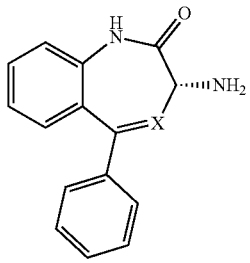
(I')

wherein X is as previously defined, with a compound of Formula (III),

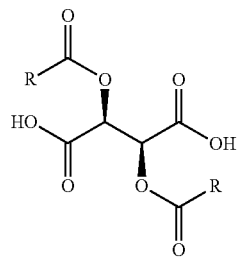
(III)

wherein R is optionally substituted phenyl, to yield a salt of Formula (IV),

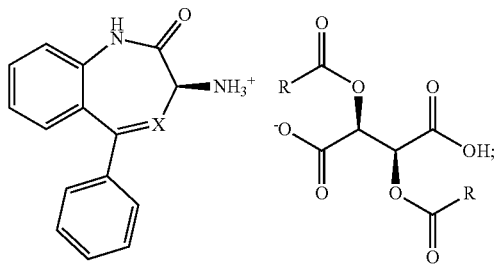
(IV)

and (2) treating the salt of Formula (IV) with a base to provide the compound of Formula (I').

In another embodiment, the present invention provides a process for the preparation of a compound of Formula (I'):

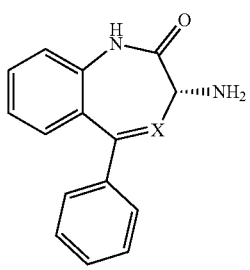
(I')

wherein X is N or CH. The process comprises the steps of
(1') reacting a compound of Formula (I),

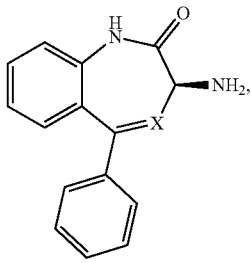
(I)

with a compound of Formula (III'),

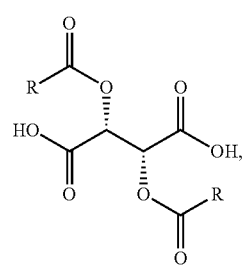
(III')

wherein R is previously defined to yield a salt of Formula (IV'),

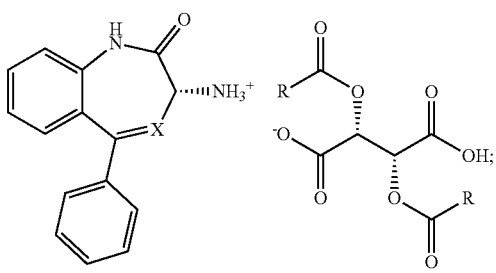
(IV')

and
(2') treating the salt of Formula (IV') with a base to provide the compound of Formula (I').

In one embodiment, the starting compound of step (1) or (1') is present in a racemic mixture with its enantiomer. In another embodiment, the starting compound of step (1) or (1') is present in a mixture with its enantiomer, wherein one of the two enantiomers is in enantiomeric excess, for example, an enantiomeric excess of at least 5, 10, 20, 30, 40, 50, 60, 70, 80 or 90%. In another embodiment, the starting compound of step (1) or (1') is present in a substantially pure form, i.e., in an enantiomeric excess of at least 90%, 95% or 99%.

Preferably, the starting compound of step (1) or step (1') is present in a racemic mixture with its enantiomer.

In one embodiment, the invention provides a method for producing a compound of Formula I, comprising the steps of
(a) reacting a racemic mixture of the compound of Formula I and a compound of Formula I', wherein X in the compound of Formula I and Formula I' are the same, with a compound of Formula (III) to yield a salt of Formula (IV); and
(b) treating the salt of Formula (IV) with a base to provide the compound of Formula (I).

In another embodiment, the invention provides a method for producing a compound of Formula I', comprising the steps of
(a') reacting a racemic mixture of the compound of Formula I' and a compound of Formula I, wherein X in the compound of Formula I and Formula I' are the same, with a compound of Formula (III') to yield a salt of Formula (IV'); and
(b') treating the salt of Formula (IV') with a base to provide the compound of Formula (I').

Preferably, the desired enantiomer is present in the product in an enantiomeric excess, for example an enantiomeric excess of at least 70%, at least 80%, or at least 85%. Preferably, the product is substantially enantiomerically pure, i.e., in an enantiomeric excess of at least 90%, at least 95% or at least 99%.

The methods of the invention surprisingly result in production of the desired enantiomer of a compound of Formula (II-0) or Formula (II),

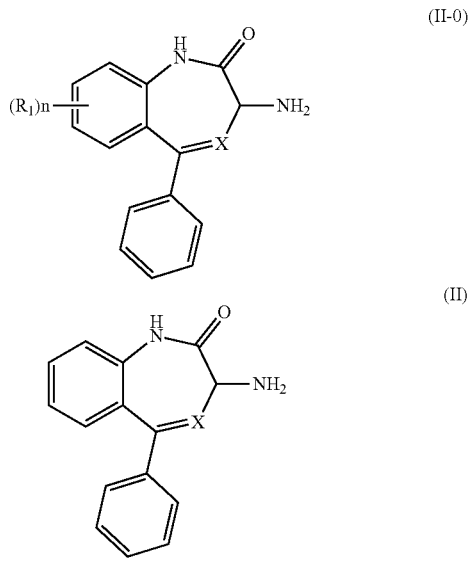

in substantially enantiomerically pure form by converting the unwanted enantiomer to the desired enantiomer. Thus, the method can be applied to the unwanted enantiomer, whether present in a substantially enantiomerically pure form or in a mixture with the desired enantiomer, such as a racemic mixture. Thus, when applied to a racemic mixture, substantially all of the starting unwanted enantiomer is converted to the desired enantiomer, resulting in a significantly greater yield of the desired enantiomer, for example, up to 75%, 85%, 90%, 95%, 99% or more of the starting compound of Formula (II-0) or Formula (II), compared to standard resolution of a racemic mixture using diastereomeric salt formation, which has a theoretical maximum yield of 50%.

In one embodiment of the compounds of Formulae (I-0), (I'-0), (II-0), (IV-0) and (IV'-0), $R_1$ is halogen, and n is 1 or 2; in another embodiment of the compounds of Formulae (I-0), (I'-0), (II-0), (IV-0) and (IV'-0), $R_1$ is F, and n is 1 or 2.

In one embodiment of the compounds of Formulae (I-0), (I'-0), (II-0), (IV-0) and (IV'-0), X is N; in another embodiment of the compounds of Formulae (I-0), (I'-0), (II-0), (IV-0) and (IV'-0), X is CH.

In one embodiment of the compounds of Formulae (I), (I'), (II), (IV) and (IV'), X is N; in another embodiment of the compounds of Formulae (I), (I'), (II), (IV) and (IV'), X is CH.

In the compounds of Formulae (III), (III'), (IV-0), (IV'-0), (IV) and (IV'), R is preferably phenyl or phenyl substituted with one or more substituents independently selected from halogen, hydroxyl, $C_1$-$C_4$-alkyl and halo-$C_1$-$C_4$-alkyl. In one preferred embodiment, R is phenyl; in another preferred embodiment R is 4-methylphenyl.

Synthetic Schemes

The present invention will be better understood in connection with Scheme 1, wherein X and R are as previously defined unless otherwise indicated; preferably, X is N, and R is

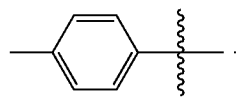

It will be readily apparent to one of ordinary skill in the art that the process of the present invention can be practiced by substitution of the indicated reactants with functionally equivalent reactants.

Scheme 1

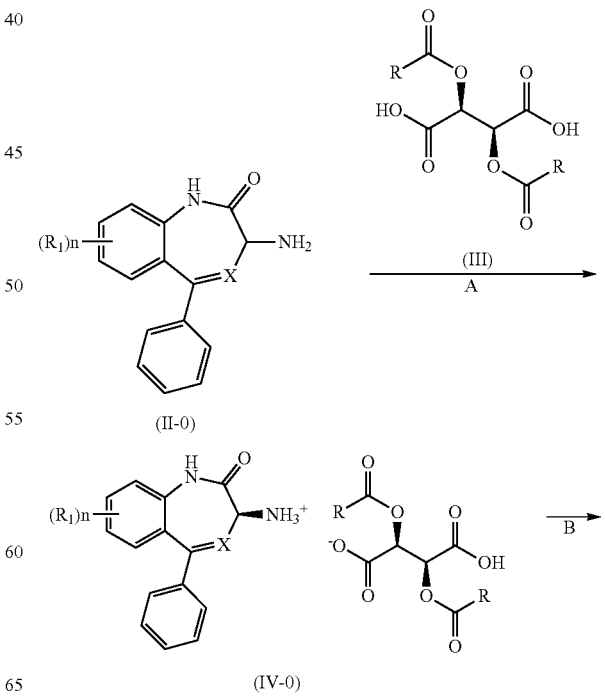

-continued

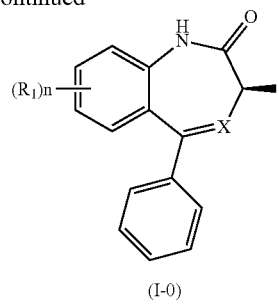

(I-0)

A compound of Formula (IV-0) is prepared, as illustrated in Step A of Scheme 1, by reacting a compound of Formula (II-0) with a compound of Formula (III) in an organic solvent, for example, at a volume of 20-100 volumes with respect to the starting amine. This process is typically carried out in a protic or aprotic solvent such as, but not limited to, acetonitrile, methanol, tetrahydrofuran, 2-methyltetrahydrofuran, ethyl acetate, 1,2-dimethoxyethane, dichloromethane, 1,4-dioxane, toluene, anisole, ethanol, acetone, N,N-dimethylformamide, N,N-dimethylacetamide, pyridine, isopropyl acetate or a combination of two or more thereof. The typical reaction temperature is about 20° C. to 30° C. or about 20° C. to about 45° C., and the reaction time is typically about 24 to 60 hours. In a preferred embodiment of the reaction, the organic solvent is 1,4-dioxane (40 volumes), the reaction temperature is about 20° C. to 25° C., and the reaction time is about 24 hours.

A compound of Formula (I-0) is prepared, as illustrated in Step B of Scheme 1, by treating a compound of Formula (IV-0) with a molar excess of an inorganic base dissolved in water. Suitable bases include, but are not limited to: sodium hydroxide, potassium carbonate, ammonium hydroxide, potassium phosphate tribasic and sodium carbonate. In certain embodiments, the compound of Formula IV-0 is treated with 1N sodium hydroxide 5 wt % potassium carbonate, 28-30% ammonium hydroxide, 10 wt % potassium phosphate (tribasic) or 5 wt % sodium carbonate. The typical reaction temperature is about 20° C. to 30° C. and the reaction time is typically about 1 to 6 hours. In a preferred embodiment of the reaction, the base is 1 N sodium hydroxide (5 volumes, ~3.2 equivalents), the reaction temperature is about 20° C. to 25° C., and the reaction time is about 4 hours.

A compound of Formula (I'-0) is prepared by using a procedure similar to that used to prepare a compound of Formula (I-0), as illustrated in Scheme 2 shown below.

Scheme 2

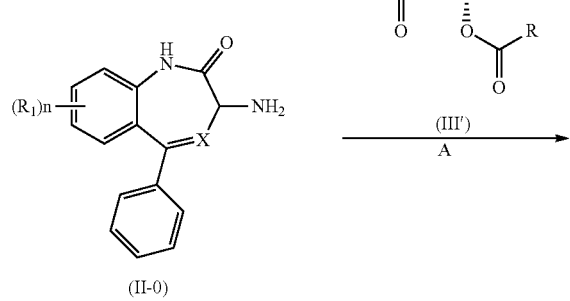

(II-0)

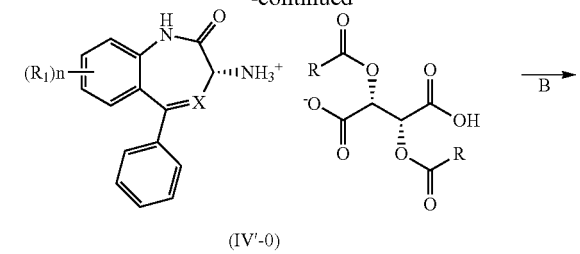

(IV'-0)

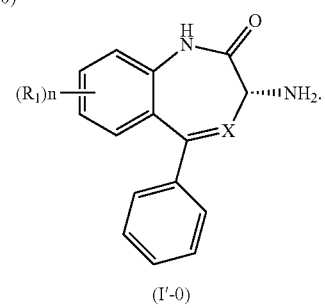

(I'-0)

Formula (II-0) in Schemes 1 and 2 represents the opposite enantiomer of the desired product, or a mixture of the two enantiomers, preferably a racemic mixture.

Definitions

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono- or polycyclic carbocyclic ring system comprising of at least one aromatic ring, including, but not limited to, phenyl, naphthyl, tetrahydronaphthyl, indanyl, and indenyl. A polycyclic aryl is a polycyclic ring system that comprises at least one aromatic ring. Polycyclic aryls can comprise fused rings, covalently attached rings or a combination thereof.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzoxazolyl, quinoxalinyl. A polycyclic heteroaryl can comprise fused rings, covalently attached rings or a combination thereof.

The term "substantially enantiomerically pure" as the term is used herein, refers to a sample of a chiral compound in which one enantiomer is present in an enantiomeric excess of at least 80%. In preferred embodiments, the enantiomeric excess is at least 90%, at least 95%, at least 98% or at least 99%.

In accordance with the invention, aromatic groups can be substituted or unsubstituted.

The term "bicyclic aryl" or "bicyclic heteroaryl" refers to a ring system consisting of two rings wherein at least one ring is aromatic; and the two rings can be fused or covalently attached.

The term "alkyl" as used herein, refers to saturated, straight- or branched-chain hydrocarbon radicals. "$C_1$-$C_4$ alkyl," "$C_1$-$C_6$ alkyl," "$C_1$-$C_8$ alkyl," "$C_1$-$C_{12}$ alkyl," "$C_2$-$C_4$ alkyl," or "$C_3$-$C_6$ alkyl," refer to alkyl groups containing from one to four, one to six, one to eight, one to twelve, 2 to 4 and 3 to 6 carbon atoms respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals.

The term "alkenyl" as used herein, refers to straight- or branched-chain hydrocarbon radicals having at least one carbon-carbon double bond by the removal of a single hydrogen atom. "$C_2$-$C_8$ alkenyl," "$C_2$-$C_{12}$ alkenyl," "$C_2$-$C_4$ alkenyl," "$C_3$-$C_4$ alkenyl," or "$C_3$-$C_6$ alkenyl," refer to alkenyl groups containing from two to eight, two to twelve, two to four, three to four or three to six carbon atoms respectively. Alkenyl groups include, but are not limited to, for example, ethenyl, propenyl, butenyl, 1-methyl-2-buten-1-yl, heptenyl, octenyl, and the like.

The term "alkynyl" as used herein, refers to straight- or branched-chain hydrocarbon radicals having at least one carbon-carbon double bond by the removal of a single hydrogen atom. "$C_2$-$C_8$ alkynyl," "$C_2$-$C_{12}$ alkynyl," "$C_2$-$C_4$ alkynyl," "$C_3$-$C_4$ alkynyl," or "$C_3$-$C_6$ alkynyl," refer to alkynyl groups containing from two to eight, two to twelve, two to four, three to four or three to six carbon atoms respectively. Representative alkynyl groups include, but are not limited to, for example, ethynyl, 1-propynyl, 1-butynyl, heptynyl, octynyl, and the like.

The term "cycloalkyl", as used herein, refers to a monocyclic or polycyclic saturated carbocyclic ring or a bi- or tri-cyclic group fused, bridged or spiro system, and the carbon atoms may be optionally oxo-substituted or optionally substituted with exocyclic olefinic double bond. Preferred cycloalkyl groups include $C_3$-$C_{12}$ cycloalkyl, $C_3$-$C_6$ cycloalkyl, $C_3$-$C_8$ cycloalkyl and $C_4$-$C_7$ cycloalkyl. Examples of $C_3$-$C_{12}$ cycloalkyl include, but not limited to, cyclopropyl, cyclobutyl, cyclopentyl, cyclohexyl, cyclopentyl, cyclooctyl, 4-methylene-cyclohexyl, bicyclo[2.2.1]heptyl, bicyclo[3.1.0]hexyl, spiro[2.5]octyl, 3-methylenebicyclo[3.2.1]octyl, spiro[4.4]nonanyl, and the like.

The term "cycloalkenyl", as used herein, refers to monocyclic or polycyclic carbocyclic ring or a bi- or tri-cyclic group fused, bridged or spiro system having at least one carbon-carbon double bond and the carbon atoms may be optionally oxo-substituted or optionally substituted with exocyclic olefinic double bond. Preferred cycloalkenyl groups include $C_3$-$C_{12}$ cycloalkenyl, $C_3$-$C_8$ cycloalkenyl or $C_5$-$C_7$ cycloalkenyl groups. Examples of $C_3$-$C_{12}$ cycloalkenyl include, but not limited to, cyclopropenyl, cyclobutenyl, cyclopentenyl, cyclohexenyl, cycloheptenyl, cyclooctenyl, bicyclo[2.2.1]hept-2-enyl, bicyclo[3.1.0]hex-2-enyl, spiro[2.5]oct-4-enyl, spiro[4.4]non-1-enyl, bicyclo[4.2.1]non-3-en-9-yl, and the like.

As used herein, the term "arylalkyl" means a functional group wherein an alkylene chain is attached to an aryl group, e.g., —$CH_2CH_2$-phenyl. The term "substituted arylalkyl" means an arylalkyl functional group in which the aryl group is substituted. Similarly, the term "heteroarylalkyl" means a functional group wherein an alkylene chain is attached to a heteroaryl group. The term "substituted heteroarylalkyl" means a heteroarylalkyl functional group in which the heteroaryl group is substituted.

As used herein, the term "alkoxy" employed alone or in combination with other terms means, unless otherwise stated, an alkyl group having the designated number of carbon atoms connected to the rest of the molecule via an oxygen atom, such as, for example, methoxy, ethoxy, 1-propoxy, 2-propoxy (isopropoxy) and the higher homologs and isomers. Preferred alkoxy are ($C_1$-$C_3$) alkoxy.

It is understood that any alkyl, alkenyl, alkynyl, cycloalkyl, heterocyclic and cycloalkenyl moiety described herein can also be an aliphatic group or an alicyclic group.

An "aliphatic" group is a non-aromatic moiety comprised of any combination of carbon atoms, hydrogen atoms, halogen atoms, oxygen, nitrogen or other atoms, and optionally contains one or more units of unsaturation, e.g., double and/or triple bonds. Examples of aliphatic groups are functional groups, such as alkyl, alkenyl, alkynyl, O, OH, NH, $NH_2$, C(O), $S(O)_2$, C(O)O, C(O)NH, OC(O)O, OC(O)NH, $OC(O)NH_2$, $S(O)_2NH$, $S(O)_2NH_2$, $NHC(O)NH_2$, NHC(O)C(O)NH, $NHS(O)_2NH$, $NHS(O)_2NH_2$, $C(O)NHS(O)_2$, $C(O)NHS(O)_2NH$ or $C(O)NHS(O)_2NH_2$, and the like, groups comprising one or more functional groups, non-aromatic hydrocarbons (optionally substituted), and groups wherein one or more carbons of a non-aromatic hydrocarbon (optionally substituted) is replaced by a functional group. Carbon atoms of an aliphatic group can be optionally oxo-substituted. An aliphatic group may be straight chained, branched, cyclic, or a combination thereof and preferably contains between about 1 and about 24 carbon atoms, more typically between about 1 and about 12 carbon atoms. In addition to aliphatic hydrocarbon groups, as used herein, aliphatic groups expressly include, for example, alkoxyalkyls, polyalkoxyalkyls, such as polyalkylene glycols, polyamines, and polyimines, for example. Aliphatic groups may be optionally substituted.

The terms "heterocyclic" or "heterocycloalkyl" can be used interchangeably and referred to a non-aromatic ring or a bi- or tri-cyclic group fused, bridged or spiro system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted or optionally substituted with exocyclic olefinic double bond. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, 2-azabicyclo [2.2.1]-heptyl, 8-azabicyclo [3.2.1]octyl, 5-azaspiro[2.5]octyl, 1-oxa-7-azaspiro[4.4]nonanyl, 7-oxooxepan-4-yl, and tetrahydrofuryl. Such heterocyclic groups may be further substituted. Heteroaryl or heterocyclic groups can be C-attached or N-attached (where possible).

It is understood that any alkyl, alkenyl, alkynyl, alicyclic, cycloalkyl, cycloalkenyl, aryl, heteroaryl, heterocyclic, aliphatic moiety or the like, described herein can also be a divalent or multivalent group when used as a linkage to connect two or more groups or substituents, which can be at the same or different atom(s). One of skill in the art can readily determine the valence of any such group from the context in which it occurs.

The term "substituted" refers to substitution by independent replacement of one, two, or three or more of the hydrogen atoms with substituents including, but not limited to, —F, —Cl, —Br, —I, —OH, $C_1$-$C_{12}$-alkyl; $C_2$-$C_{12}$-alkenyl, $C_{2-12}$-alkynyl, —$C_3$-$C_{12}$-cycloalkyl, protected hydroxy, —$NO_2$, —$N_3$, —CN, —$NH_2$, protected amino, oxo, thioxo, —NH—$C_1$-$C_{12}$-alkyl, —NH—$C_2C_8$-alkenyl, —NH—$C_2$-$C_8$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$- alkyl, —O—$C_2$-$C_8$-alkenyl, —O—$C_2$-$C_8$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)-heteroaryl, —C(O)-heterocycloalkyl, —CONH$_2$, —CONH—$C_1$-$C_{12}$-alkyl, —CONH—$C_2$-$C_8$-alkenyl, —CONH—$C_2$-$C_8$-alkynyl, —CONH—$C_3$-$C_{12}$-cycloalkyl, —CONH-aryl, —CONH-heteroaryl, —CONH-heterocycloalkyl, —OCO$_2$—$C_1$-$C_{12}$-alkyl, —OCO$_2$—$C_2$-$C_8$-alkenyl, —OCO$_2$—$C_2$-$C_8$-alkynyl, —OCO$_2$—$C_3$-$C_{12}$-cycloalkyl, —OCO$_2$-aryl, —OCO$_2$-heteroaryl, —OCO$_2$-heterocycloalkyl, —CO$_2$—$C_1$-$C_{12}$ alkyl, —CO$_2$—$C_2$-$C_8$ alkenyl, —CO$_2$—$C_2$-$C_8$ alkynyl, CO$_2$—$C_3$-$C_{12}$-cycloalkyl, —CO$_2$-aryl, CO$_2$-heteroaryl, CO$_2$-heterocyloalkyl, —OCONH$_2$, —OCONH—$C_1$-$C_{12}$-alkyl, —OCONH—$C_2$-$C_8$-alkenyl, —OCONH—$C_2$-$C_8$-alkynyl, —OCONH—$C_3$-$C_{12}$-cycloalkyl, —OCONH-aryl, —OCONH-heteroaryl, —OCONH-heterocyclo-alkyl, —NHC(O)H, —NHC(O)—$C_1$-$C_{12}$-alkyl, —NHC(O)—$C_2$-$C_8$-alkenyl, —NHC(O)—$C_2$-$C_8$-alkynyl, —NHC(O)—$C_3$-$C_{12}$-cycloalkyl, —NHC(O)-aryl, —NHC(O)-heteroaryl, —NHC(O)-heterocyclo-alkyl, —NHCO$_2$—$C_1$-$C_{12}$-alkyl, —NHCO$_2$—$C_2$-$C_8$-alkenyl, —NHCO$_2$—$C_2$-$C_8$-alkynyl, —NHCO$_2$—$C_3$-$C_{12}$-cycloalkyl, —NHCO$_2$-aryl, —NHCO$_2$-heteroaryl, —NHCO$_2$-heterocycloalkyl, —NHC(O)NH$_2$, —NHC(O)NH—$C_1$-$C_{12}$-alkyl, —NHC(O)NH—$C_2$-$C_8$-alkenyl, —NHC(O)NH—$C_2$-$C_8$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)NH$_2$, —NHC(S)NH—$C_1$-$C_{12}$-alkyl, —NHC(S)NH—$C_2$-$C_8$-alkenyl, —NHC(S)NH—$C_2$-$C_8$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—$C_1$-$C_{12}$-alkyl, —NHC(NH)NH—$C_2$-$C_8$-alkenyl, —NHC(NH)NH—$C_2$-$C_8$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_8$-alkenyl, —NHC(NH)—$C_2$-$C_8$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_8$-alkenyl, —C(NH)NH—$C_2$-$C_8$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_8$-alkenyl, —S(O)—$C_2$-$C_8$-alkynyl, —S(O)—$C_3$-$C_{12}$-cycloalkyl, —S(O)-aryl, —S(O)-heteroaryl, —S(O)-heterocycloalkyl, —SO$_2$NH$_2$, —SO$_2$NH—$C_1$-$C_{12}$-alkyl, —SO$_2$NH—$C_2$-$C_8$-alkenyl, —SO$_2$NH—$C_2$-$C_8$-alkynyl, —SO$_2$NH—$C_3$-$C_{12}$-cycloalkyl, —SO$_2$NH-aryl, —SO$_2$NH-heteroaryl, —SO$_2$NH-heterocycloalkyl, —NHSO$_2$—$C_1$-$C_{12}$-alkyl, —NHSO$_2$—$C_2$-$C_8$-alkenyl, —NHSO$_2$—$C_2$-$C_8$-alkynyl, —NHSO$_2$—$C_3$-$C_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_8$-alkenyl, —S—$C_2$-$C_8$-alkynyl, —S—$C_3$-$C_{12}$-cycloalkyl, —S-aryl, —S-heteroaryl, —S-heterocycloalkyl, or methylthiomethyl. It is understood that the aryls, heteroaryls, alkyls, cycloalkyls and the like can be further substituted.

The term "halo" or halogen" alone or as part of another substituent, as used herein, refers to a fluorine, chlorine, bromine, or iodine atom.

The term "optionally substituted", as used herein, means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

The term "hydrogen" includes hydrogen and deuterium. In addition, the recitation of an atom includes other isotopes of that atom so long as the resulting compound is pharmaceutically acceptable.

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis*, 3rd edition, John Wiley & Sons, New York (1999). Examples of amino protecting groups include, but are not limited to, methoxycarbonyl, t-butoxycarbonyl, 9-fluorenyl-methoxycarbonyl, benzyloxycarbonyl, and the like.

The term "protected amino," as used herein, refers to an amino group protected with an amino protecting group as defined above.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether, 1,4-dioxane. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, NY, 1986.

The term "protic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, NY, 1986.

Combinations of substituents and variables envisioned by this invention are only those that result in the formation of stable compounds. The term "stable," as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or crystallization. As can be appreciated by the skilled artisan, further methods of synthesizing the compounds of the formula herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, 2$^{nd}$ Ed. Wiley-VCH (1999); T. W. Greene and P. G. M. Wuts, *Protective Groups in Organic Synthesis*, 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The term "subject," as used herein, refers to an animal. Preferably, the animal is a mammal. More preferably, the mammal is a human. A subject also refers to, for example, dogs, cats, horses, cows, pigs, guinea pigs, fish, birds and the like.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

Suitable concentrations of reactants used in the synthesis processes of the invention are 0.01 M to 10 M, typically 0.05 M to 1 M. Suitable temperatures include −78° C. to 250° C., typically −78° C. to 150° C., more typically −78° C. to 100° C., still more typically 0° C. to 40° C. Reaction vessels are preferably made of any material which does not substantial interfere with the reaction. Examples include glass, plastic or stainless steel. The pressure of the reaction can advantageously be operated at atmospheric pressure. The atmospheres include, for example, air, for oxygen and water insensitive reactions, or nitrogen or argon, for oxygen or water sensitive reactions.

The term "in situ," as used herein, refers to use of an intermediate in the solvent or solvents in which the intermediate was prepared without removal of the solvent.

Abbreviations

Abbreviations which may be used in the descriptions of the scheme and the examples that follow are:
HBr for hydrobromic acid;
AcOH for acetic acid;
Brine for sodium chloride solution in water;
DME for 1,2-dimethoxyethane;
DMF for N,N-dimethylformamide;
DMAc for N,N-dimethylacetamide;
DMSO for dimethyl sulfoxide;
EtOH for ethanol;
$K_2CO_3$ for potassium carbonate;
MeOH for methanol;
MTBE for methyl tert-butyl ether;
NaCl for sodium chloride;
$Na_2CO_3$ sodium carbonate;
NaOH for sodium hydroxide;
NMP for N-Methyl-2-pyrrolidone
o/n for overnight;
i-PrOAc for isopropyl acetate;
Ph for phenyl;
r.t. for room temperature;
THF for tetrahydrofuran;
h for hours;
g for grams;
mmol for millimoles;
equ for molar equivalents;
mL for milliliters;
° C. for degrees celcius;
HPLC for high performance chromatography;
wt % for weight percent;
area % for area percent;
N for normality
M for molarity
$H_2O$ for water;
% for percentage;
KF for Karl Fisher;
min for minutes;

All other abbreviations used herein, which are not specifically delineated above, shall be accorded the meaning which one of ordinary skill in the art would attach.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

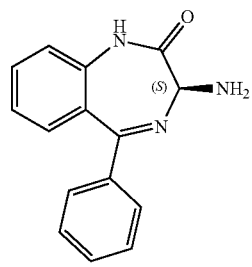

Step 1A. Preparation of Compound 3: (S)-3-amino-5-phenyl-1,3-dihydro-2H-benzo [e][1,4]diazepin-2-one (2S,3S)-2,3-bis((4-methylbenzoyl)oxy)succinate Method 1

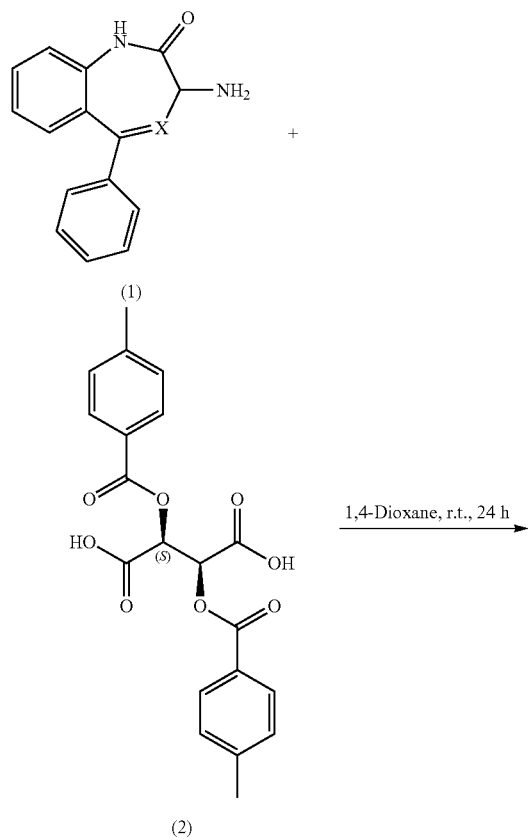

filtered off under vacuum, washed with 1,4-dioxane (2×25 mL, 2×2.5 volumes) and aspirated for ≥2 hours then dried in the vacuum oven at 35±5° C. for ≥16 hours to afford compound 3, (S)-3-amino-5-phenyl-1,3-dihydro-2H-benzo [e][1,4]diazepin-2-one (2S,3S)-2,3-bis((4-methylbenzoyl)oxy)succinate (32.6 g, >100%) as an off white solid. By $^1$H NMR the solid is a 1:1 ratio of amine:tartaric acid containing approximately 19 wt % dioxane. The salt is taken directly into the next step and neutralized assuming a quantitative conversion. Chiral purity=99.33:0.67 area %/(S):(R).

Method 1-Large Scale

A 30 L jacketed reactor equipped with an overhead stirrer and temperature probe was flushed with nitrogen then charged with compound 1, 3-amino-5-phenyl-1,3-dihydro-2H-benzo [e][1,4]diazepin-2-one (200 g, 796 mmol, 1 equiv.) as a racemic mixture and 1.4-dioxane (4 L, 20 volumes) followed by compound 2, (+)—O,O'-Di-p-toluoyl-D-tartaric acid (317 g, 796 mmol, 1 equiv.) and 1,4-dioxane (4 L, 20 volumes). The reaction was stirred at 25±2° C. for 24 hours under nitrogen and monitored by chiral HPLC. The solid was filtered off under vacuum, washed with 1,4-dioxane (2×500 mL, 2×2.5 volumes) and aspirated for ≥2 hours then dried in the vacuum oven at 35±5° C. for ≥16 hours to afford compound 3, (S)-3-amino-5-phenyl-1,3-dihydro-2H-benzo [e][1,4]diazepin-2-one (2S,3S)-2,3-bis ((4-methylbenzoyl)oxy)succinate (520 g, >100%) as a white solid. By $^1$H NMR the solid is a 1:1 ratio of amine:tartaric acid containing approximately 14.5 wt % dioxane. The salt is taken directly into the next step and neutralized assuming a quantitative conversion. Chiral purity=99.09:0.91 area %/(S):(R).

Method 2

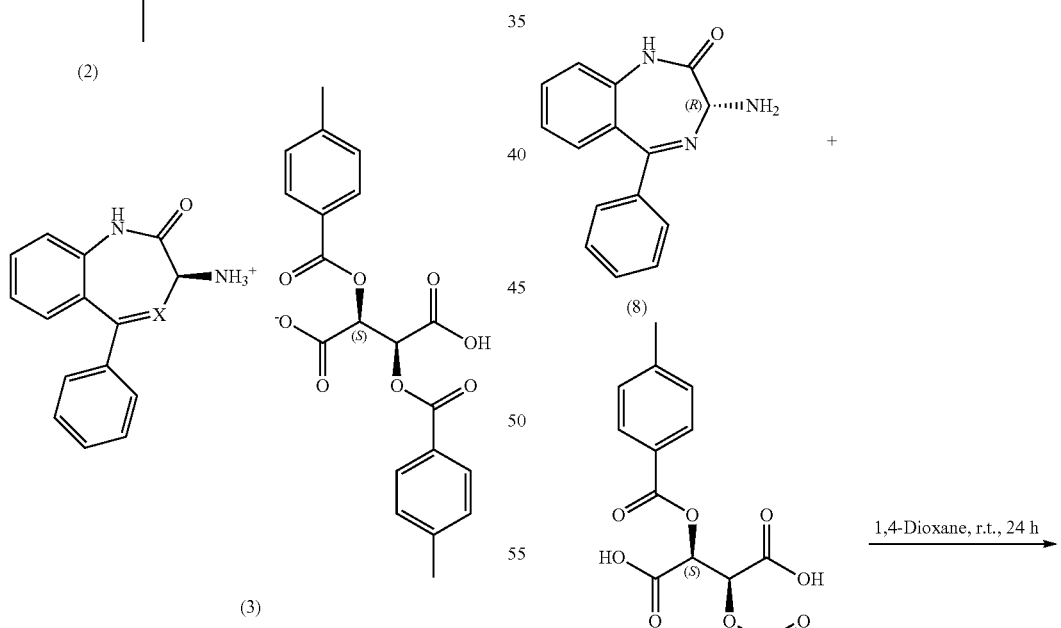

A 1 L round bottom flask equipped with an overhead stirrer and temperature probe was charged with compound 1, 3-amino-5-phenyl-1,3-dihydro-2H-benzo[e][1,4]diazepin-2-one (10 g, 39.8 mmol, 1 equiv.) as a racemic mixture, compound 2, (+)—O,O'-Di-p-toluoyl-D-tartaric acid (15.37 g, 39.8 mmol, 1 equiv.) and 1,4-dioxane (400 ml, 40 volumes). The reaction was stirred at 20±5° C. for 24 hours under air and monitored by chiral HPLC. The solid was -continued

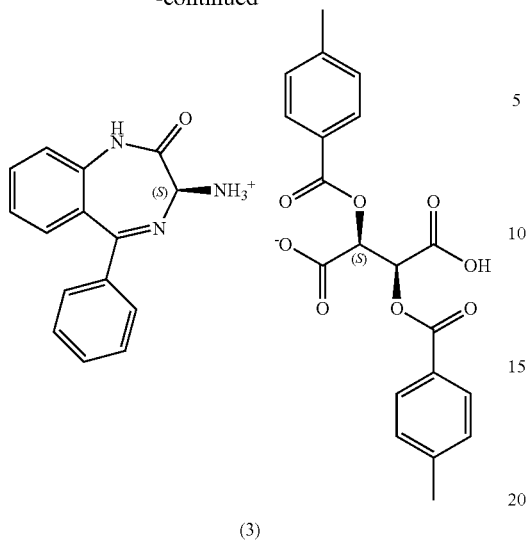

(3)

An 8 mL scintillation vial equipped with a magnetic stirrer was charged with compound 8, (R)-3-amino-5-phenyl-1,3-dihydro-2H-benzo[e][1,4]diazepin-2-one (100 mg, 0.398 mmol, 1 equiv.), compound 2, (+)—O,O'-Di-p-toluoyl-D-tartaric acid (154 mg, 0.398 mmol, 1 equiv.) and 1,4-dioxane (4 ml, 40 volumes). The reaction was stirred at 20±5° C. for at least 24 hours under air and monitored by chiral HPLC. The solid was filtered off under vacuum to afford compound 3, (S)-3-amino-5-phenyl-1,3-dihydro-2H-benzo[e][1,4]diazepin-2-one (2S,3S)-2,3-bis((4-methylbenzoyl) oxy)succinate (294 mg, >100%) as an off white solid. The chiral purity of the isolated solid=99.89:0.11 area %/(S):(R).

Method 3

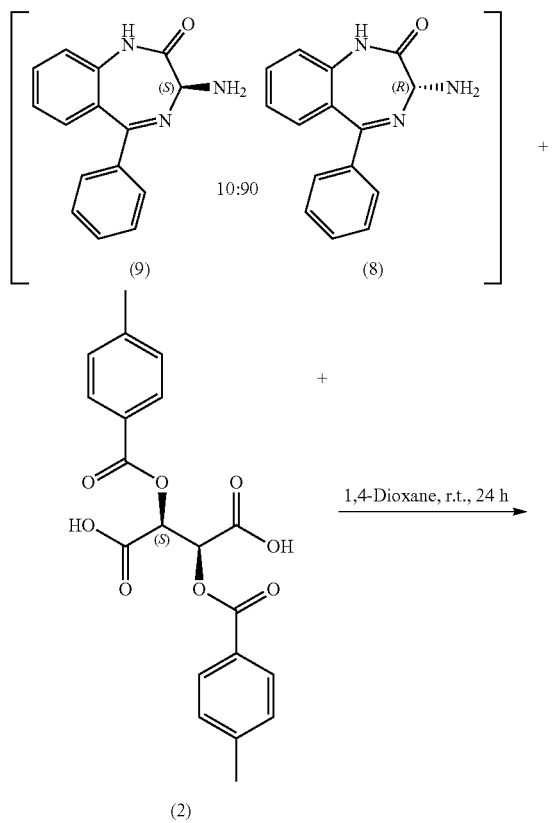

-continued

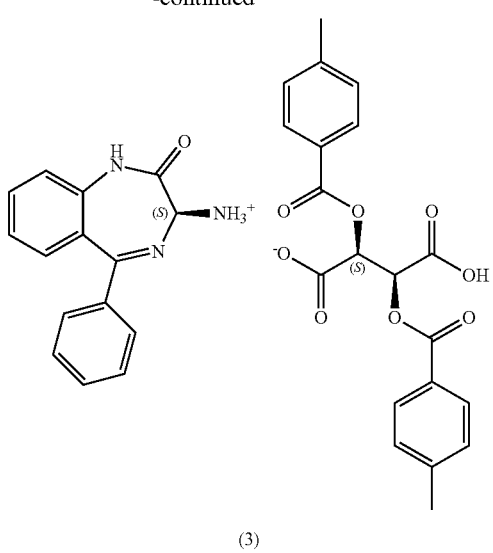

(3)

An 8 mL scintillation vial equipped with a magnetic stirrer was charged with a mixture of compound 8, (R)-3-amino-5-phenyl-1,3-dihydro-2H-benzo[e][1,4]diazepin-2-one (90 mg, 0.358 mmol, 0.9 equiv.), compound 9, (S)-3-amino-5-phenyl-1,3-dihydro-2H-benzo[e][1,4]diazepin-2-one (10 mg, 0.04 mmol, 0.1 equiv.), compound 2, (+)—O,O'-Di-p-toluoyl-D-tartaric acid (154 mg, 0.398 mmol, 1 equiv.) and 1,4-dioxane (4 ml, 40 volumes). The reaction was stirred at 20±5° C. for at least 24 hours under air and monitored by chiral HPLC. The solid was filtered off under vacuum to afford compound 3, (S)-3-amino-5-phenyl-1,3-dihydro-2H-benzo[e][1,4]diazepin-2-one (2S,3S)-2,3-bis((4-methylbenzoyl)oxy)succinate (288 mg, >100%) as an off white solid. The chiral purity of the isolated solid=99.75:0.25 area %/(S):(R).

Step 1B. Preparation of Example 1: (S)-3-amino-5-phenyl-1,3-dihydro-2H-benzo [e][1,4]diazepin-2-one

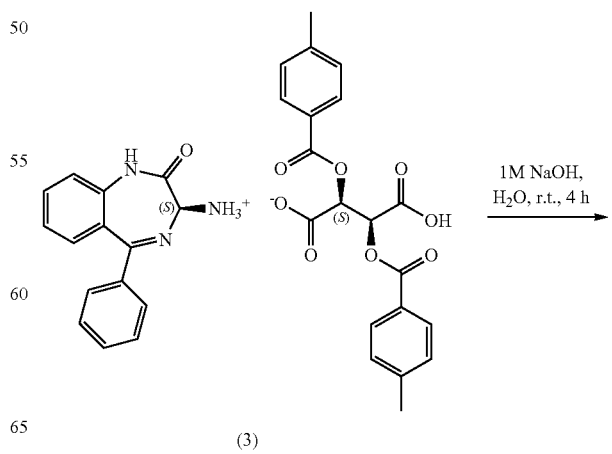

23
-continued

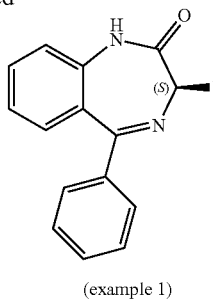

(example 1)

A 400 mL round bottom flask equipped with an overhead stirrer and temperature probe was charged with compound 3, (S)-3-amino-5-phenyl-1,3-dihydro-2H-benzo[e][1,4]diazepin-2-one (2S,3S)-2,3-bis((4-methylbenzoyl)oxy)succinate (25.0 g, 39.2 mmol, 1 equ) and 1 M sodium hydroxide (125 mL, 5 volumes). The suspension was stirred at 20±5° C. for 4 hours under air. The solid was filtered off under vacuum, washed with water (3×50 mL–3×2 volumes) aspirated for ≥1 hour then dried in the vacuum oven at 35±5° C. for ≥16 hours to afford (S)-3-amino-5-phenyl-1,3-dihydro-2H-benzo[e][1,4]diazepin-2-one (7.34 g, 74%) as a white solid. $^1$H NMR (400 MHz, DMSO-$d_6$) δ 10.66 (s, 1H), 7.58 (ddd, J=8.6, 7.1, 1.6 Hz, 1H), 7.54–7.38 (m, 5H), 7.26 (dt, J=8.0, 1.7 Hz, 2H), 7.19 (td, J=7.5, 1.2 Hz, 1H), 4.22 (s, 1H). LCMS m/z=252.2 [M+H]$^+$. HPLC purity=99.6% a/a. Chiral purity=99.46 (ee %). KF=0.28%. Optical rotation, $[\alpha]_D^{25}$=−200.0° (c=0.1, MeOH).

Step 1B Large Scale

A 5 L round bottom flask equipped with an overhead stirrer and temperature probe was charged with compound 3, (S)-3-amino-5-phenyl-1,3-dihydro-2H-benzo[e][1,4]diazepin-2-one (2S,3S)-2,3-bis ((4-methylbenzoyl)oxy)succinate (507 g, 0.795 mol, 1 equiv.) and 1 M sodium hydroxide (2.54 L, 2.544 mol, 3.2 equiv., or 5 volumes). The suspension was stirred at 20±5° C. for 5 hours under nitrogen and monitored by chiral HPLC. The solid was filtered off under vacuum, washed with water (3×1 L–3×2 volumes) and aspirated for ≥1 hour then dried in the vacuum oven at 35±5° C. for ≥16 hours to afford (S)-3-amino-5-phenyl-1,3-dihydro-2H-benzo [e][1,4]diazepin-2-one (185 g, 93%) as an off white solid. $^1$H NMR (400 MHz, DMSO-$d_6$) δ 10.66 (s, 1H), 7.58 (ddd, J=8.5, 7.1, 1.6 Hz, 1H), 7.53–7.38 (m, 5H), 7.26 (dt, J=8.1, 1.5 Hz, 2H), 7.19 (ddd, J=8.1, 7.1, 1.2 Hz, 1H), 4.22 (s, 1H). LCMS m/z=235.1 [M−NH$_2$]$^+$ and 274.4 [M+Na]$^+$. HPLC purity=100.0% a/a. Chiral purity=98.3 (ee %). KF=0.2%. Optical rotation, $[\alpha]_D^{23}$=−178.0° (c=0.132, MeOH).

Example 2

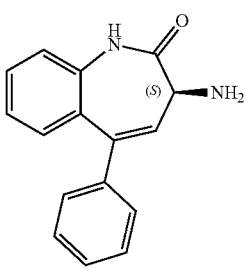

24
Step 2A. Preparation of Compound 5

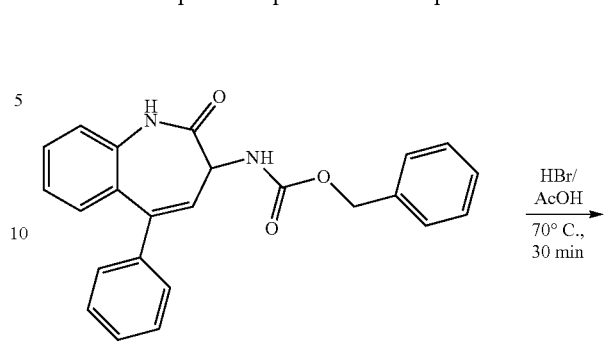

Compound 4 was prepared using a procedure described in U.S. Pat. No. 6,528,505B1, the contents of which are incorporated herein by reference in their entirety. A solution of Compound 4, benzyl (2-oxo-5-phenyl-2,3-dihydro-1H-benzo[b]azepin-3-yl)carbamate (11 g, 28 mmol) in 33% HBr/HOAc (34 equ of HBr) as a racemic mixture was stirred at 70° C. for 30 mins and then cooled to room temperature. Hexane (100 mL) was added to the flask and solids were filtered out. The mother liquor was basified with NH$_3$H$_2$O and more solids were collected. The solids were combined and dried to give compound 5 as a purple solid (6.7 g, 94%) ESI-MS m/z: 251.15 [M+H]$^+$. $^1$H NMR (400 MHz, DMSO-$d_6$) δ 3.68 (s, 1H), 5.89 (m, 1H), 6.30 (m, 2H), 7.06 (m, 1H), 7.08-7.61 (m, 8H), 10.49 (s, 1H).

Steps 2B and 2C. Preparation of Example 2: (S)-3-amino-5-phenyl-1,3-dihydro-2H-benzo [b]azepin-2-one

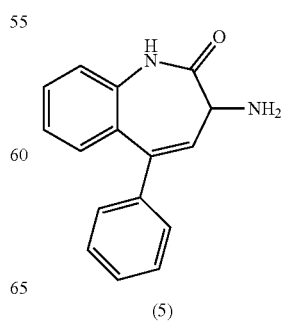

+

(5)

-continued

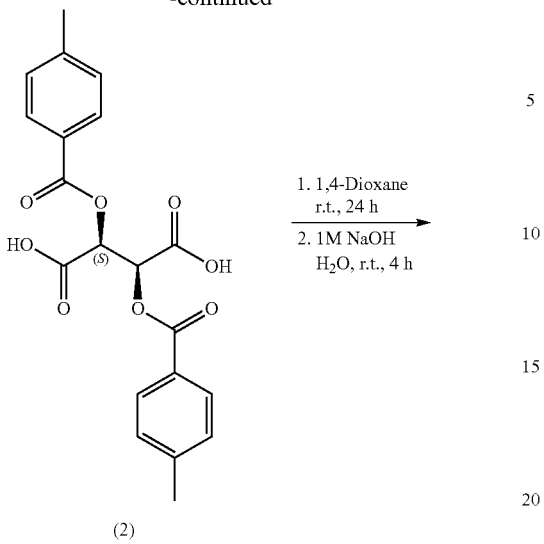

(2)

1. 1,4-Dioxane r.t., 24 h
2. 1M NaOH H₂O, r.t., 4 h

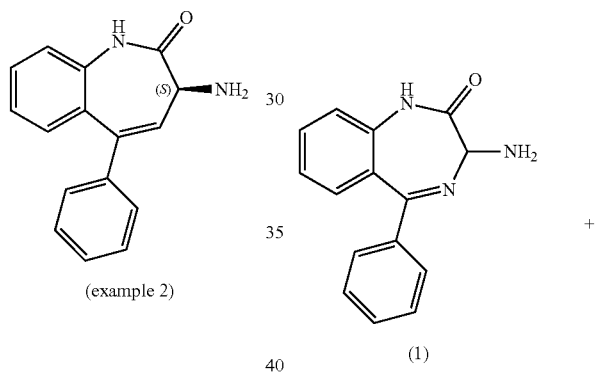

(example 2)

A 250 mL round bottom flask equipped with a magnetic stirrer was charged with 3-amino-5-phenyl-1,3-dihydro-2H-benzo[b]azepin-2-one (racemic, 2.05 g, 8.19 mmol), compound 2, (+)—O,O'-Di-p-toluoyl-D-tartaric acid (3.16 g, 8.19 mmol) and 1,4-dioxane (82 ml). The reaction was stirred at 20±5° C. for 24 hours under air and monitored by chiral HPLC. The white solid was filtered off under vacuum, aspirated for ≥2 hours then transferred into a 50 mL round bottom flask. 1 M sodium hydroxide (25 mL, 12.5 volumes) was added to the flask along with a magnetic stirrer. The suspension was stirred at 20±5° C. for 4 hours under air. The solid was filtered off under vacuum, washed with water (3×10 mL) aspirated for ≥1 hour then dried under vacuum at room temperature for ≥16 hours to afford (S)-3-amino-5-phenyl-1,3-dihydro-2H-benzo[b]azepin-2-one (1.5 g, 5.99 mmol, 73.2% yield) as a white solid. $^1$H NMR (400 MHz, DMSO-$d_6$) δ 10.33 (s, 1H), 7.40–7.32 (m, 4H), 7.24–7.20 (m, 3H), 7.1–7.05 (m, 2H), 5.88 (d, J=5.4 Hz, 1H), 3.38 (d, J=5.5 Hz, 1H). LCMS m/z=251.8 [M+H]$^+$. HPLC purity=99.4% a/a. Chiral purity=99.0 (ee %).

Example 3

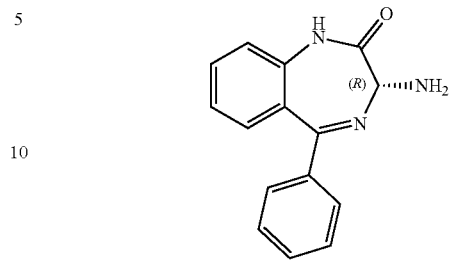

Step 3A. Preparation of Compound 7: (R)-3-amino-5-phenyl-1,3-dihydro-2H-benzo [e][1,4]diazepin-2-one (2R,3R)-2,3-bis((4-methylbenzoyl)oxy)succinate (1) +

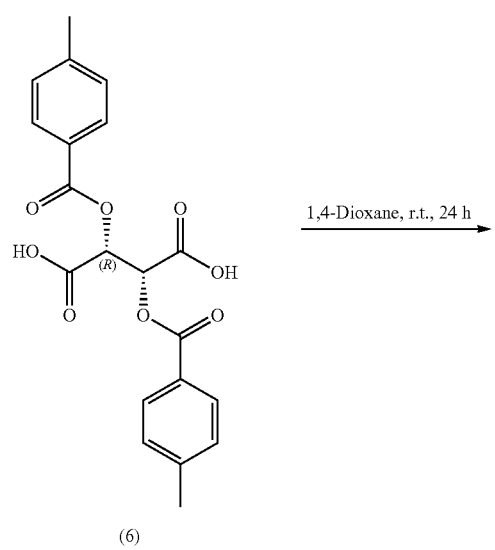

(6)

1,4-Dioxane, r.t., 24 h

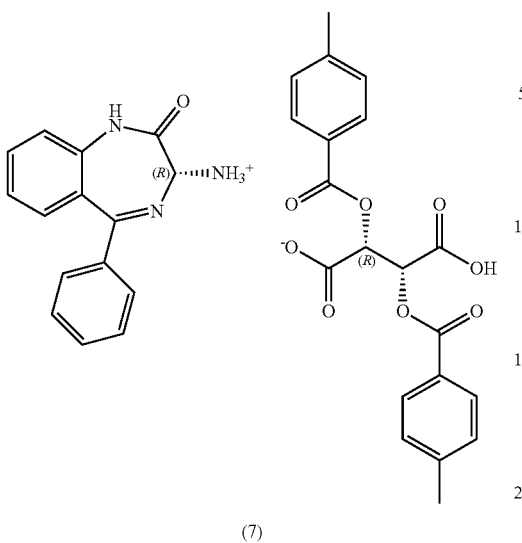

(7)

A 1 L round bottom flask equipped with an overhead stirrer and temperature probe was charged with compound 1,3-amino-5-phenyl-1,3-dihydro-2H-benzo[e][1,4]diazepin-2-one (racemic; 10 g, 39.8 mmol, 1 equiv.), compound 6, (−)—O,O'-Di-p-toluoyl-L-tartaric acid, 97% (15.85 g, 39.8 mmol, 1 equiv.) and 1,4-dioxane (400 ml, 40 volumes). The reaction was stirred at 20±5° C. for 24 hours under air and monitored by chiral HPLC. The solid was filtered off under vacuum, aspirated for ≥2 hours then dried in the vacuum oven at 35±5° C. for ≥16 hours to afford compound 7, (R)-3-amino-5-phenyl-1,3-dihydro-2H-benzo[e][1,4]diaz-epin-2-one (2R,3R)-2,3-bis ((4-methylbenzoyl)oxy)succi-nate (25.3 g, 99%) as an off white solid. By $^1$H NMR the solid is a 1:1 ratio of amine:tartaric acid containing approximately 16 wt % dioxane. The salt is taken directly into the next step and neutralized assuming a quantitative conversion. Chiral purity 0:100 area %/(S):(R).

Step 3B. Preparation of Example 3: (R)-3-amino-5-phenyl-1,3-dihydro-2H-benzo [e][1,4]diazepin-2-one

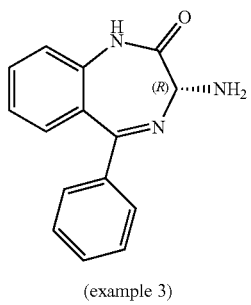

(example 3)

A 400 mL round bottom flask equipped with an overhead stirrer and temperature probe was charged with compound 7, (R)-3-amino-5-phenyl-1,3-dihydro-2H-benzo[e][1,4]diaz-epin-2-one (2R,3R)-2,3-bis((4-methylbenzoyl)oxy)succi-nate (25.0 g, 39.2 mmol, 1 equ) and 1 M sodium hydroxide (125 mL, 5 volumes). The suspension was stirred at 20±5° C. for 4 hours under air. The solid was filtered off under vacuum, washed with water (3×50 mL−2 volumes) aspirated for ≥1 hour then dried in the vacuum oven at 35±5° C. for ≥16 hours to afford (R)-3-amino-5-phenyl-1,3-dihydro-2H-benzo[e][1,4]diazepin-2-one (9.09 g, 92%) as a white solid. $^1$H NMR (400 MHz, DMSO-d$_6$) δ 10.66 (s, 1H), 7.58 (ddd, J=8.6, 7.2, 1.6 Hz, 1H), 7.54–7.38 (m, 5H), 7.26 (dt, J=8.0, 1.8 Hz, 2H), 7.19 (td, J=7.5, 1.2 Hz, 1H), 4.22 (s, 1H). LCMS m/z=252.0 [M+H]$^+$. HPLC purity=99.7% a/a. Chiral purity=99.8 (ee %). KF=0.30%. Optical rotation, $[α]_D^{25}$=+187.7° (c=1.1, MeOH).

Example 4

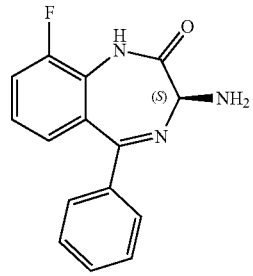

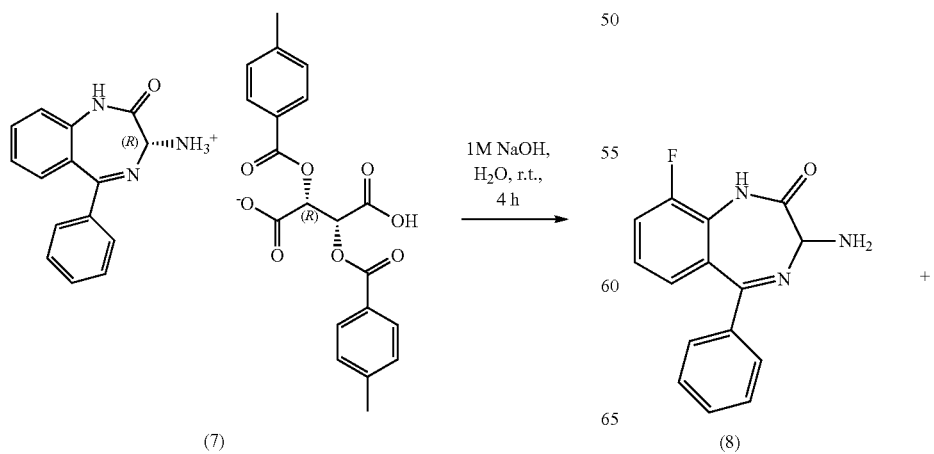

(7)     (8)

-continued

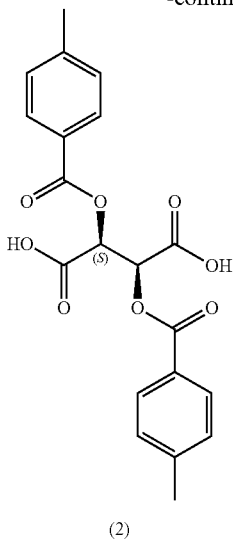

1) 1,4-Dioxane/ r.t/o/n
2) 1M NaOH/ r.t./4 h
3) 4M HCl (2)

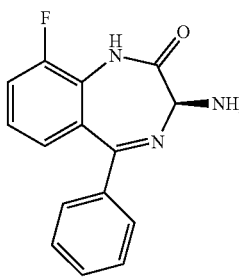

(example 4)

A 50 mL round bottom flask equipped with a magnetic stirrer was charged with compound 8, 3-amino-9-fluoro-5-phenyl-1,3-dihydro-2H-benzo[e][1,4]diazepin-2-one (racemic mixture, 250 mg, 0.928 mmol), compound 2, (2S,3S)-2,3-bis((4-methylbenzoyl)oxy)succinic acid (359 mg, 0.928 mmol) and Dioxane (9284 µl). The reaction was stirred at room temperature overnight. The white solid was filtered off under vacuum, aspirated for 30 mins then transferred into a 50 mL round bottom flask. 1 M sodium hydroxide (3.5 mL) was added to the flask along with a magnetic stirrer. The suspension was stirred at room temperature for 4 hours under air. To the homogeneous solution, 10 drops of 4 M HCl (aq) was added, which precipitated a white solid. The solid was filtered off under vacuum, washed with water (3×10 mL) aspirated for ≥1 hour to afford example 4, (S)-3-amino-9-fluoro-5-phenyl-1,3-dihydro-2H-benzo[e][1,4]diazepin-2-one (170 mg, 0.631 mmol, 68.0% yield). 96% ee.

While this invention has been particularly shown and described with references to preferred embodiments thereof, it will be understood by those skilled in the art that various changes in form and details may be made therein without departing from the scope of the invention encompassed by the appended claims.

What is claimed:

1. A process for the preparation of a compound of Formula (I-0):

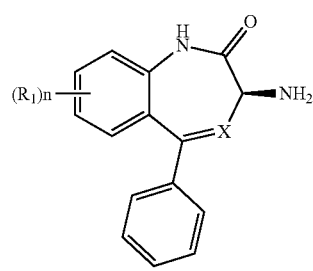

(I-0)

wherein X is N; $R_1$ is halogen, CN or optionally substituted $C_1$-$C_3$ alkyl; and n is 0, 1, 2 or 3;
said process comprising:
(a) reacting a compound of Formula (I'-0),

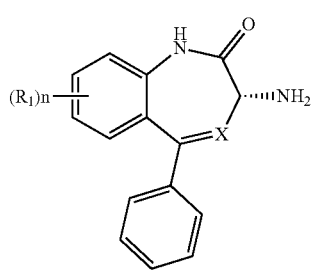

(I'-0)

with a compound of Formula (III),

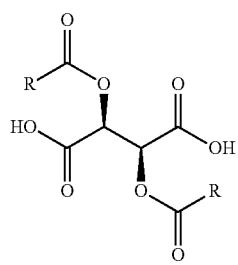

(III)

wherein R is optionally substituted phenyl, in a solvent selected from acetonitrile, methanol, tetrahydrofuran, 2-methyltetrahydrofuran, ethyl acetate, 1,2-dimethoxyethane, dichloromethane, 1,4-dioxane, toluene, anisole, ethanol, acetone, N,N-dimethylformamide, N,N-dimethylacetamide, pyridine and isopropyl acetate, or a combination of two or more thereof and at a temperature of 20° C. to 45° C., to yield a compound of Formula (IV-0),

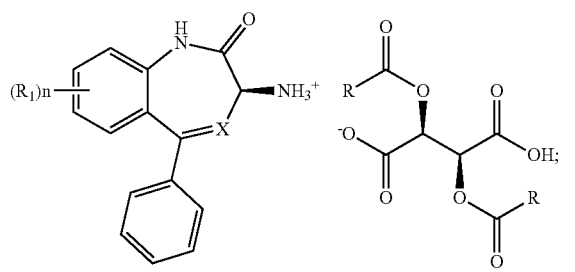

provided that said reaction takes place in the absence of an aromatic aldehyde; and (b) treating the compound of Formula (IV-0) with a base to provide the compound of Formula (I-0).

2. The process of claim 1, wherein R is

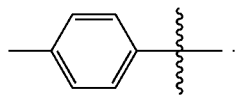

3. The process of claim 1, wherein step (a) is carried out in a solvent selected from tetrahydrofuran and 1,4-dioxane.

4. The process of claim 1, wherein in step (b), the base is sodium hydroxide, potassium carbonate, ammonium hydroxide, potassium phosphate tribasic or sodium carbonate.

5. The process of claim 4, wherein the base is 1N sodium hydroxide, 5 wt % potassium carbonate, 28-30% ammonium hydroxide, 10 wt % potassium phosphate tribasic or 5 wt % sodium carbonate.

6. The process of claim 1, wherein in step (a) the compound of Formula (I'-0) is present in a mixture with its enantiomer.

7. The process of claim 6, wherein the mixture is a racemic mixture.

8. The process of claim 1, wherein n is 0.

9. The process of claim 1, wherein step (a) is conducted at a temperature of 20° C. to 30° C.

10. The process of claim 1, wherein step (a) is conducted for 24 to 60 hours.

11. The process of claim 1, wherein step (a) is conducted for about 24 hours in dioxane at a temperature of 20° C. to 25° C.

12. The process of claim 1, wherein R is phenyl or phenyl substituted with one or more substituents independently selected from halogen, hydroxyl, $C_1$-$C_4$-alkyl and halo-$C_1$-$C_4$-alkyl.

13. The process of claim 1, wherein R is phenyl.

14. The process of claim 1, wherein n is 1 or 2 and each $R_1$ is halogen.

15. The process of claim 14, wherein each $R_1$ is fluorine.

* * * * *